(12) United States Patent
Ellis et al.

(10) Patent No.: US 7,214,225 B2
(45) Date of Patent: May 8, 2007

(54) CONNECTOR

(76) Inventors: Julian Ellis, c/o Ellis Developments Limited, 68 Carlton Road, Nottingham, NG3 2AP (GB); Alan McLeod, c/o Pearsalls Limited, Tancred Street, Taunton, Somerset, TA1 1RY (GB); Peter Butcher, c/o Ellis Developments Limited, 68 Carlton Road, Nottingham, NG3 2AP (GB)

( * ) Notice: Subject to any disclaimer, the term of this patent is extended or adjusted under 35 U.S.C. 154(b) by 215 days.

(21) Appl. No.: 10/399,016

(22) PCT Filed: Oct. 11, 2001

(86) PCT No.: PCT/GB01/04524

§ 371 (c)(1),
(2), (4) Date: Jul. 10, 2003

(87) PCT Pub. No.: WO02/30306

PCT Pub. Date: Apr. 18, 2002

(65) Prior Publication Data

US 2004/0024403 A1 Feb. 5, 2004

(51) Int. Cl.
*A61B 17/58* (2006.01)
(52) U.S. Cl. .......................... 606/60; 606/151; 606/61

(58) Field of Classification Search ................. 606/61, 606/60, 69, 70, 71, 151, 152, 153, 155, 156
See application file for complete search history.

(56) References Cited

U.S. PATENT DOCUMENTS

| 5,108,397 A * | 4/1992 | White ........................ 606/60 |
| 6,033,429 A * | 3/2000 | Magovern ................... 606/216 |
| 6,368,326 B1 * | 4/2002 | Dakin et al. ................ 606/103 |
| 2001/0027319 A1 * | 10/2001 | Ferree ......................... 606/61 |

FOREIGN PATENT DOCUMENTS

| FR | 2710520 A1 * | 4/1995 |
| WO | WO 02/30324 | 4/2002 |

* cited by examiner

*Primary Examiner*—Eduardo C. Robert
*Assistant Examiner*—James L. Swiger
(74) *Attorney, Agent, or Firm*—Jonathan D. Spangler

(57) ABSTRACT

A connector comprising at least one pair of apertures for receiving a fastener, such as a screw, a load bearing filament extending continuously along a predefined circuitous path which extends between and around each of the apertures of said pair of apertures. The load bearing filament extends around each aperture to define multiple aperture forming strands of said load bearing filaments. The multiple aperture forming strands of the load bearing filament are bound together around each aperture by binding filaments in order to constrain relative lateral movement between the aperture forming multiple strands and to define the shape of each aperture.

19 Claims, 8 Drawing Sheets

CONNECTOR

FIELD OF THE INVENTION

The present invention concerns a connector, in particular but not exclusively, a connector for use in surgery for connecting bones or bone parts to one another.

BACKGROUND OF THE INVENTION

When connecting bones or bone parts to one another using a connector, it is desirable for the connector to be capable of transmitting loads between the connected bone parts in a predetermined manner. This may be done to constrain separation between the bone parts by a predetermined amount and also constrain to a predetermined amount, the amount of torsional movement between the bone parts.

SUMMARY OF THE INVENTION

According to one aspect of the present invention there is provided a connector comprising at least one pair of apertures for receiving a fixation means, such as a screw or a toggle, a load bearing filament extending continuously along a predefined circuitous path which extends between and around each of the apertures of said pair of apertures, said load bearing filament extending around each aperture to define multiple aperture forming strands of said load bearing filaments, said aperture forming multiple strands of said load bearing filament being bound together around each aperture by binding filaments in order to constrain relative lateral movement between said aperture forming multiple strands and to define the shape of each aperture.

DESCRIPTION OF THE PREFERRED EMBODIMENTS

Figure 1:
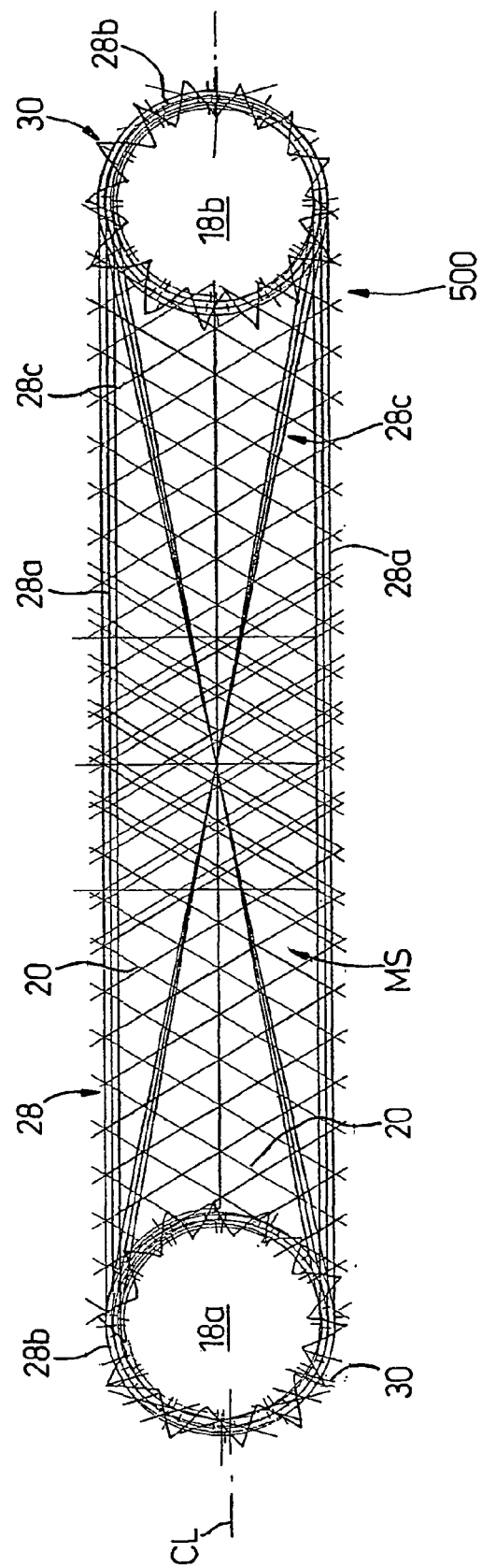
FIG. 1 is a schematic plan view of a connector according to a first embodiment of the present invention.

Referring initially to FIG. 1, there is shown a connector 500 according to a first embodiment of the present invention.

The connector 500 includes a pair of apertures 18$\underline{a}$, 18$\underline{b}$ and a load bearing filament 28 which follows a circuitous path which extends continuously around and between the apertures 18$\underline{a}$, 18$\underline{b}$. In use, the connector is attached to say a pair of bone parts by a fixation means, such as a screw or a toggle, located in the apertures 18a, 18b.

The filament 28 is preferably laid along said circuitous path for a plurality of complete circuits so as to define multiple strands 28$\underline{a}$, 28$\underline{b}$ and 28$\underline{c}$.

In FIG. 1, the multiple strands 28$\underline{a}$ define aperture connecting strands which extend in a direction parallel to the central axis $C_L$ joining the pair of apertures 18$\underline{a}$, 18$\underline{b}$; strands 28b define aperture forming strands which extend continuously around each aperture 18a, 18b; and strands 28c define aperture connecting strands which extend diagonally between the apertures 18$\underline{a}$, 18$\underline{b}$.

Figure 2A:
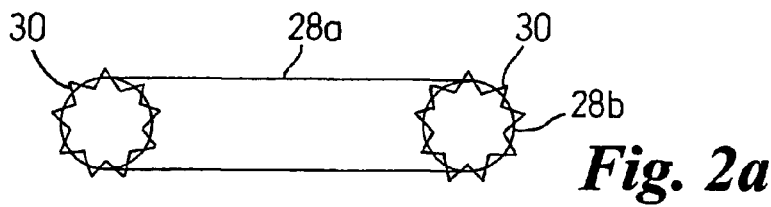
FIGS. 2a to 2c are diagrammatic plan views of modifications to the first embodiment of the present invention.
Figure 2B:
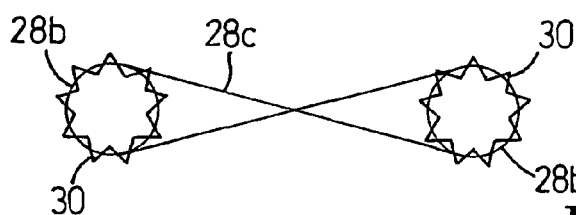
Figure 2C:
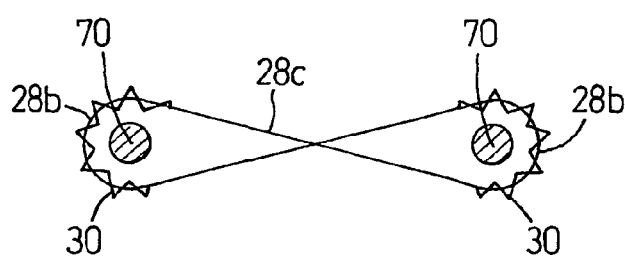

As indicated in FIG. 2a, 2b and 2c the circuitous path may be varied in order to change the configuration of the connector 500.

In FIG. 2a, the diagonal strands 28c are omitted such that the apertures 18$\underline{a}$, 18$\underline{b}$ defined by the strands 28b are connected by strands 28a only.

Alternatively, as indicated in FIG. 2b, strands 28a are omitted such that strands 28b are connected by diagonal strands 28c only.

In the embodiment of FIG. 2c, strands 28b only partially extend around the outer periphery of each aperture 18a, 18b.

With this embodiment, strands 28a may also be included such that apertures 18$\underline{a}$, 18$\underline{b}$ are connected by strands 28$\underline{a}$ and 28$\underline{c}$; or alternatively strands 28a may be provided instead of strands 28c.

Binding filaments 30 are provided which secure the strands 28b together in order to constrain relative movement therebetween around each aperture 18a, 18b and also define the shape of each aperture 18a, 18b.

The binding filaments 30 thereby act to maintain integrity of each aperture 18$\underline{a}$, 18$\underline{b}$ when a fixation means, such as a bone screw, is to be inserted through the aperture during attachment of the connector; the binding filaments 30 also act to maintain integrity of each aperture 18a, 18b when a tensile load is applied between the apertures 18$\underline{a}$, 18$\underline{b}$ during use.

Accordingly, a bone screw may be inserted directly into apertures 18a, 18b without the need for an intermediary support such as a washer or collar.

In the embodiments of FIGS. 1, 2a and 2b the binding filaments 30 preferably extend around the entire periphery of each aperture 18$\underline{a}$, 18$\underline{b}$.

In the embodiment of FIG. 2c, the binding filaments 30 extend about the outer periphery only of the apertures 18$\underline{a}$, 18$\underline{b}$.

Figure 3:
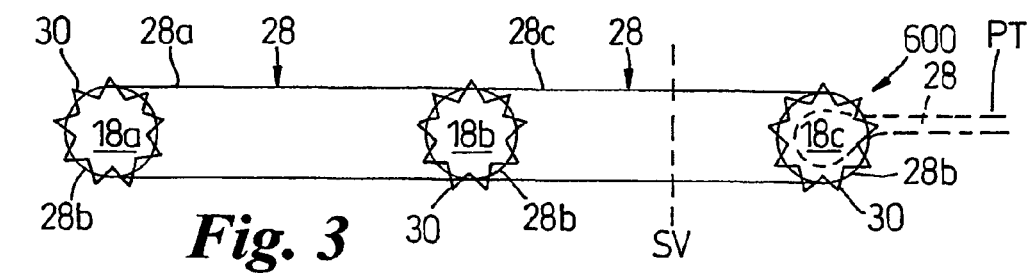
FIG. 3 is a diagrammatic plan view of a connector according to a second embodiment of the present invention.

In FIG. 3 a further embodiment 600 is illustrated which comprises a first pair of apertures 18$\underline{a}$, 18$\underline{b}$ linked with a second pair of apertures 18b, 18c. The apertures 18a, 18b; 18b, 18c in each pair are connected to one another and defined by the load bearing filament 28. As with the first embodiment, the load bearing filament 28 extends along a circuitous path between and around the apertures 18a, 18b and 18c so as to connect them by multiple strands 28a and/or 28c and define them by strands 28b. In the embodiment illustrated in FIG. 3, strands 28$\underline{a}$ only are provided.

Preferably the circuitous path along which the load bearing filament 28 extends enables the strands 28a (and/or 28c if provided) to be severed (as indicated by line $S_y$) between one pair of apertures 18$\underline{b}$, 18$\underline{c}$ without adversely affecting the connection between the other pairs of apertures 18$\underline{a}$, 18$\underline{b}$.

The connection defined by the load bearing filament 28 between each pair of apertures may thus be considered as a chain defined by a series of chain links.

Figure 4:
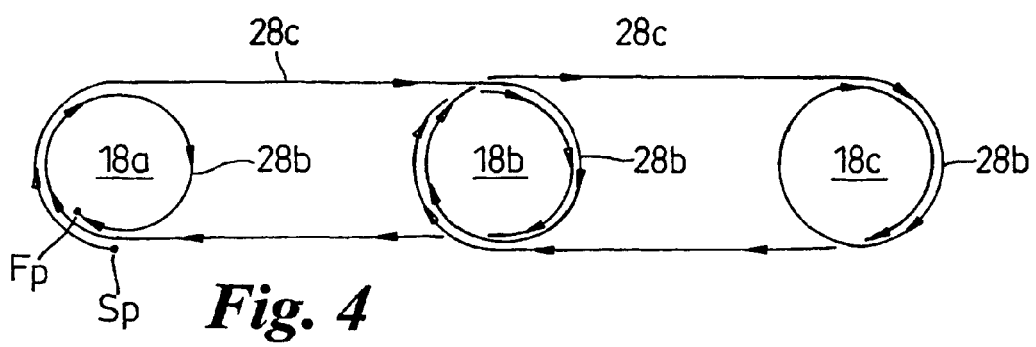
FIG. 4 diagrammatically illustrates a first example of formation of the second embodiment.

An illustration of a circuitous path for the load bearing filament 28 in order to form the embodiment 600 is illustrated in FIG. 4.

The starting point of the path is $S_p$ and the finishing point is $F_p$. The load bearing yarn 28 is laid along the path in the direction indicated by the arrows.

Initially the filament is laid partially around the periphery of aperture 18*a*, then extends to and completely around aperture 18*b* then extends to and completely around aperture 18*c* and then extends to and around aperture 18*b*. It then extends to and completely round aperture 18*a*.

This produces single strands 28*a* and multiple strands 28*b*.

If desired the load bearing yarn 28 may be laid along this circuitous path several times in order to provide multiple strands 28*a*.

The multiple strands 28*b* are secured together by binding filaments 30 after the load bearing filament 28 has been laid along the circuitous path.

Figure 8:
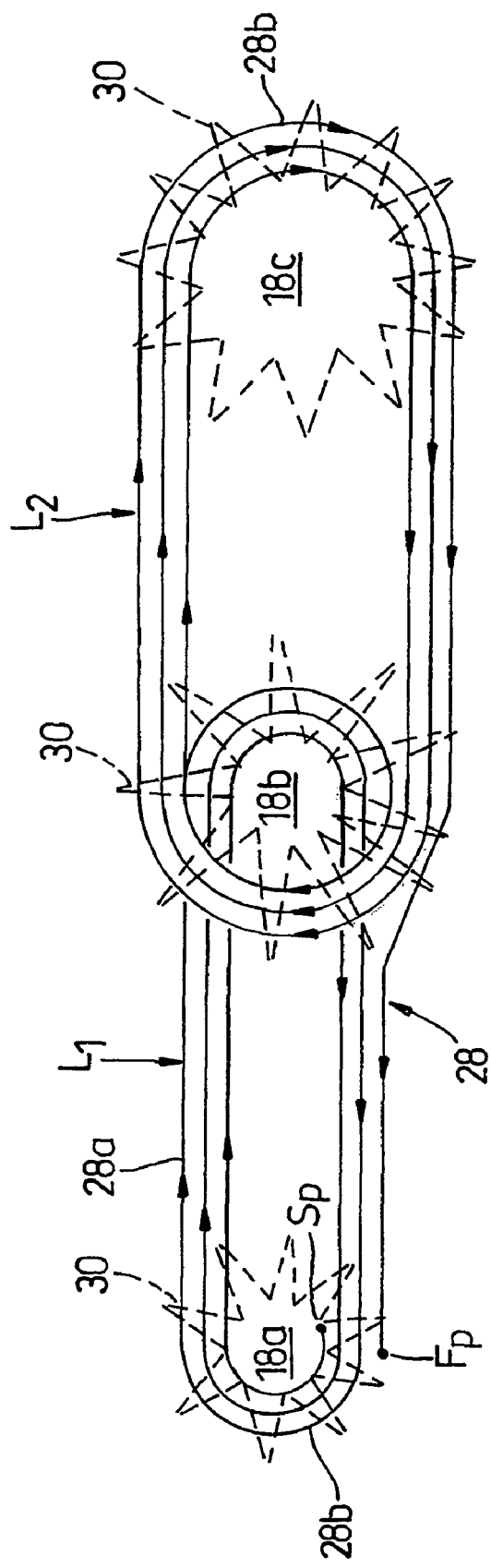
FIG. 8 is a second example of formation of the second embodiment.

An alternative circuitous path for forming the embodiment 600 of FIG. 4 is illustrated in FIG. 8.

Initially the filament is laid partially around the periphery of 18*a*, then extends to and partially around the aperture 18*a*. Thus the filament 28 initially follows a first substantially elliptical path which extends about apertures 18*a*, 18*b*. The filament 28 is repeatedly laid along the first elliptical path for a predetermined number of times so as to define multiple strands 28*a* and multiple strands 28*b*. These collectively form a first chain link or loop $L_1$.

After the filament 28 has been laid along the first elliptical path for said predetermined number of times, it is then laid along a second substantially elliptical path for another predetermined number of times; the second elliptical path extending around the next pair of apertures 18*b*, 18*c*. This forms a second chain link or loop $L_2$.

After completing laying of the filament 28 around the second elliptical path for said predetermined number of times, the filament 28 is laid along side the strand of the first elliptical path which extend between apertures 18*a*, 18*b*. In this way, the same number of strands 28*a* are laid inbetween each pair of apertures 18*a*, 18*b*; and 18*b*; 18*c*.

After laying of the load bearing filament 28, the multiple aperture forming strands 28*b* are secured together by binding filaments 30 which extend around each aperture (as shown in broken lines).

When the surgical connector includes multiple strands 28*a* or 28*c*, it is important that the tensile loads inbetween a pair of anchorage apertures be shared as equally as possible between the individual strands making up each multiple strand 28*a*, and/or 28*c*.

This is particularly important when, in use, the aperture interconnecting strands 28*a*, and/or 28*c*, extend between a pair of apertures located on different planes which are also possibly of different orientation.

In order to achieve, as best as possible an equal sharing of tensile loads in each individual strand which makes up a multiple aperture interconnecting strand 28*a*, and/or 28*c*, the filament 28 when being laid along the circuitous path is anchored at selected anchorage locations $A_L$ to a support backing sheet MS so that each individual strand extends between a series of anchorage locations spaced along its length and so is constrained thereby to follow a predefined path.

Preferably the filament is laid along the circuitous path by an embroidery machine having a base cloth support table movable in two dimensions in response to a patterning control for accurately positioning the base cloth relative to the sewing needle of the machine. The sewing needle is positioned on one side of the base cloth (referred to as the needle side of the base cloth) and when actuated penetrates through the base cloth to project from the opposite side of the base cloth (referred to as the looper side) in order to co-operate with a looper which supplies a looper thread to form a sewn stitch with thread supplied by the needle.

Preferably, the filament 28 is supplied as the looper thread and so is laid on the looper side of the base cloth. The stitches formed between the filament 28 and needle thread define the anchorage locations along the length of the filament.

Figure 9A:
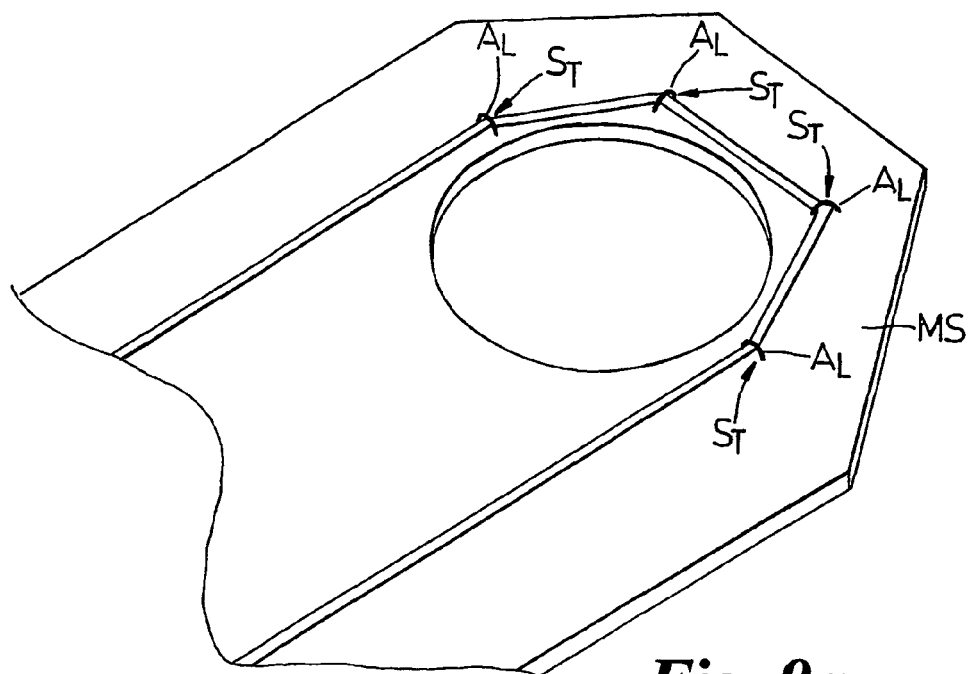
FIGS. 9a to 9d schematically illustrate laying of load bearing filaments to form multiple aperture forming strands.
Figure 9B:
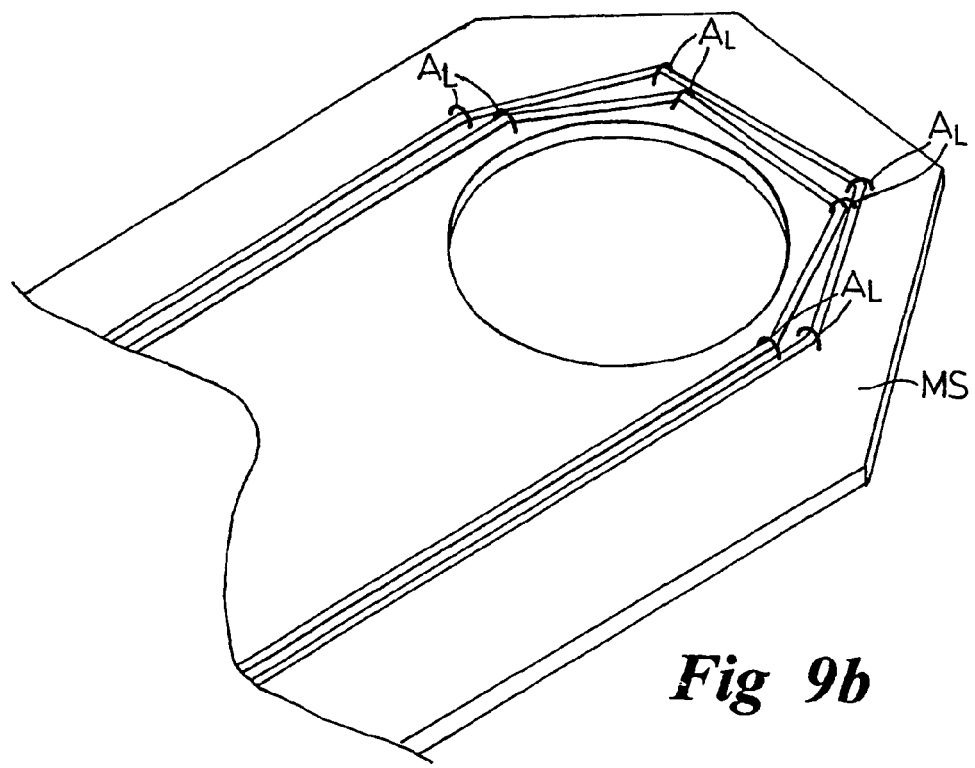
Figure 9C:
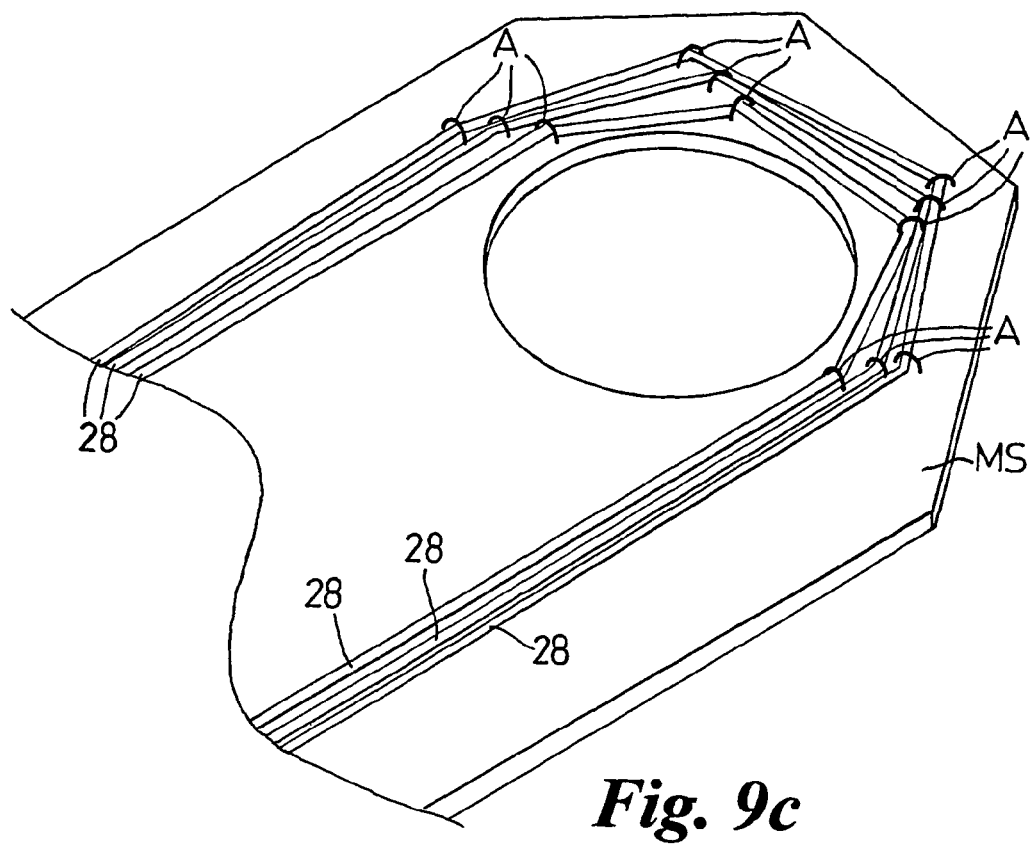

As illustrated in FIGS. 9*a* to 9*c* the thread $S_T$ supplied to the sewing needle is preferably chosen so as to be much finer than the filament 28 such that the filament 28 remains substantially flat with the base cloth and is not pulled through toward the needle side of the base cloth. In this way the filament 28 remains substantially straight between each adjacent anchorage location defined by the stitches.

The length of the filament 28 inbetween each adjacent stitch is therefore accurately predetermined.

It will be appreciated that as an alternative, the heavier load bearing filament 28 could be supplied by the needle and the finer thread $S_T$ be supplied by the looper.

Preferably a minimal number of stitches are formed along the filament 28 defining the aperture interconnecting strands 28*a* and/or 28*c*.

When laying the filament 28 around an aperture, the anchorage locations are arranged to define a polygonal path (see FIG. 9). The number of anchorage locations $A_L$ and the spacing between adjacent locations are chosen, bearing in mind the diametric size of the aperture to be formed and the bending capability of the filament 28.

It is envisaged that the number of anchorage locations around an aperture is at least 3.

In addition to laying the filament 28 to define predetermined lengths inbetween adjacent anchorage locations, the anchorage locations for adjacent individual strands 28*b* around the aperture to be formed are positioned such that adjacent strands are nested in contact together in a predefined manner to resist lateral movement of the strands 28*b* relative to one another when a tensile load is applied between a pair of adjacent apertures.

In addition, all the individual strands 28*b* extending about a given aperture are bound together by sewn stitches formed from binding filaments 30. Preferably the binding filaments 30 are sewn in a zig-zag manner around each aperture so as to enclose the strands 28*b*.

In this way, in use, the strands 28*b* remain in substantially the same position relative to one another as when they were laid and so each retains a predefined position around the aperture and so all individual strands making up the multiple aperture interconnecting strands 28*a* and/or 28*c* also retain their predefined length when placed under a tensile load inbetween adjacent apertures 18 and so the tensile load is substantially equally shared by the individual aperture interconnecting strands.

As shown in FIGS. 9*b*, 9*c*, the anchorage locations around $A_L$ the aperture to be formed for one strand 28*b* are off-set from the anchorage locations of the neighbouring strand 28*b*. This enables the strands 28*b* to be closely arranged.

Figure 9D:
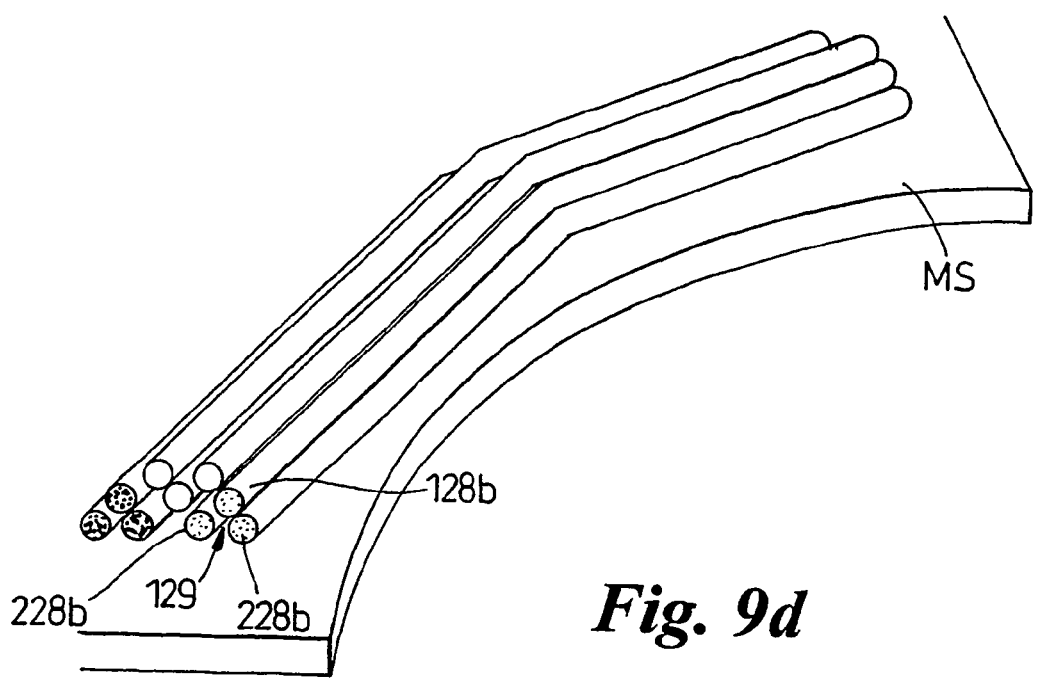

Preferably, as shown in FIG. 9*d*, the individual strands 28*b* may be arranged on top of one another such that a strand 128*b* is seated within a groove 129 formed inbetween a pair of adjacent strands 228*b*. In this way, it is possible to stack strands 28*b* on top of one another in a disciplined and predefined manner to obtain a relatively large number of nested strands in a relatively small space which co-operate with one another to resist relative lateral movement.

When stacking strands of filament 28 on top of one another, it is preferred to lay the strands closer to the aperture first and then successively lay strands on the outer side of the laid strands. This enables strands to be laid upon one another without reducing the desired diameter of the aperture.

In the embodiment illustrated in FIG. 1, the load bearing filament 28 is supported on a backing sheet MS which is preferably a mesh-like fabric formed from interconnected sewn stitches formed from yarns 20.

The backing sheet MS primarily serves the purpose of retaining the load bearing filament 28 in a disciplined fashion for facilitating handling of the connector during implantation; it is not intended to accommodate tensile loadings between adjacent apertures. Accordingly, yarns 20 may be of a lighter weight than the filament 28.

As discussed above, the sewn stitches are preferably formed using embroidery techniques which produce stitches above and below the load bearing filament 28 and so enwrap the load bearing filament 28 within the mesh-like fabric. Normally the embroidery will be performed on a base cloth which may be soluble so as to enable the base cloth to be dissolved away prior to implantation. In such a case, the sewn stitches defining the mesh-like fabric then constitute the backing sheet.

Alternatively, the base cloth may be retained to define the backing sheet MS, this may be a knitted or woven fabric or a sheet of material such as plastics to which the load bearing filament 28 is attached, by for example suitable stitching. The backing sheet MS whether formed by a sheet or a mesh-like fabric, or a knitted or woven fabric may be dissolvable so that once the backing sheet MS dissolves away it leaves apertures 18a, 18b connected solely by the load bearing filaments.

The load bearing filaments may be laid along the circuitous path by passing around pegs 70 (illustrated in FIGS. 2c) with the strands 28b then being subsequently secured by either stitching filaments 30 or wrapping filaments 30 around the strands 28b (eg. using whipping techniques).

The load bearing filament 28 may be a textile yarn such as a polyester braided thread as used for sutures. Preferably the suture thread has a diametric size between 0.2 to 0.5 mm, preferably about 0.35 mm. Other types of yarn could also be used, for example polypropylene, polyethylene, polyamide.

Preferably, the number of strands making up the multiple strands 28z, 28b and/or 28c vary between 2 to 15; more preferably vary between 5 to 10.

Instead of a textile yarn, other types of filamentary material may be used, e.g. wire of suitable metals such as a SMA (Shape Memory Alloy), aramid fibres, glass strands.

The load bearing yarn may be formed from a material which slowly dissolves after implantation. Suitable examples are polylactic acid or alginate fibres.

In general it is envisaged that any filament having the desired load bearing capabilities and flexibility for bending to lie along the desired circuitous path may be used.

Preferably, the yarn 20 and/or binding filament 30 is a textile yarn, preferably a polyester braided thread. The yarn 20 and/or binding filament 30 is preferably a suture braid thread having a diametric size between 0.1 to 0.2 mm, preferably about 0.15 mm.

It will be appreciated that the principle of connecting adjacent pairs of apertures 18a, 18b by laying a load bearing filament 28 along a circuitous path enables many different types of connector to be constructed which are of the desired shapes and sizes tailored for a particular application.

As indicated in broken lines in FIG. 3, it is envisaged that the connector of the invention may incorporate a pulling tail or cord $P_T$ which is longitudinally aligned with the row of apertures 18a, 18b and 18c.

In use, a surgeon is able to secure the connector using aperture 18a and then pull on the pulling tail $P_T$ in order to tension the connector before securing the connector using apertures 18b and/or 18c. The connector is therefore pre-tensioned before final fixing.

Preferably the pulling tail $P_T$ is formed by a plurality of strands of load bearing yarn 28 which are laid so as to form a continuation of the chain formation. After installation the pulling tail $P_T$ may be cut away. Alternatively, the pulling tail may be used as a tie for providing additional anchorage of the connector.

Figure 5:
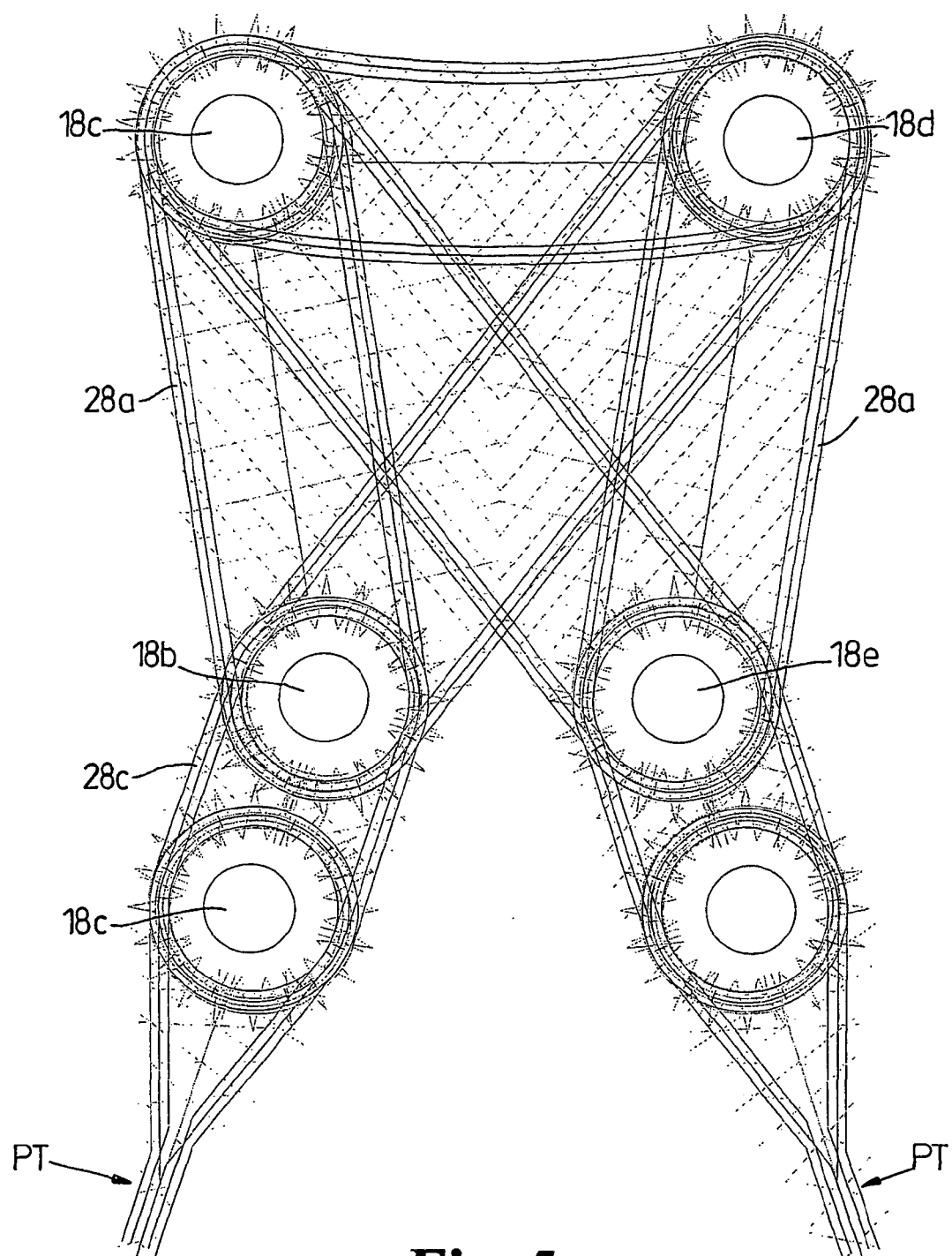
FIG. 5 is a diagrammatic plan view of a third embodiment of the present invention.

By way of example, in FIG. 5 a connector 300 suitable for attachment to a vertebrae is illustrated.

In connector 300, the load bearing filament 28, in effect, creates a chain-link between apertures 18a, 18b and a pair of chain links between apertures 18b, 18c and 18b, 18d. This means that loads are spread evenly from aperture 18b to both apertures 18c, 18d.

Aperture 18c is connected to three apertures 18b, 18d and 18e by chain-links defined by strands 28a such that loads are evenly distributed from aperture 18c to apertures 18b, 18d and 18e.

Figure 6:
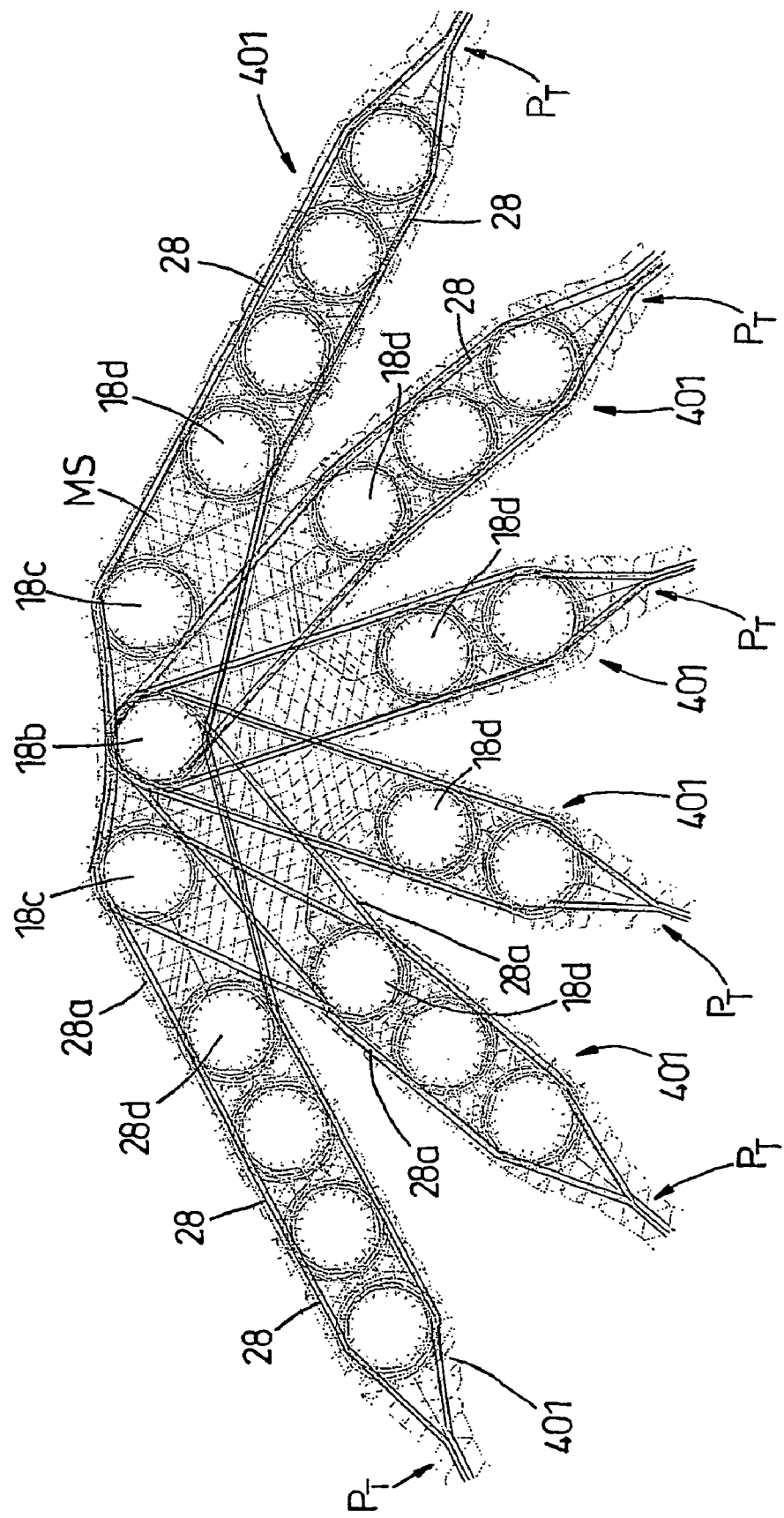
FIG. 6 is a diagrammatic plan view of a fourth embodiment of the present invention.

A further example is illustrated in FIG. 6 which is a connector 400 suitable for use as an anterior spinal plate.

The connector 400 includes six arms 401 each formed by a series of apertures 18 interconnected by chain-links formed by the filaments 28. The arms 401 radiate from three main fixation apertures 18a, 18b and 18c. These apertures 18a, 18b and 18c are attached to the LS vertebra of a patient and the arms 401 are attached to the sacrum. Due to the multiplicity of arms 401 and the plurality of apertures 18 they contain, it is possible to obtain good anchorage on the complex, three dimensional shape of the sacrum.

Preferably, as shown in FIG. 6, the end aperture 18d of each of the outer pair of arms 401 is preferably interconnected to at least two of the apertures 18a–18c in order to provide a desired spread of loadings.

Figure 7:
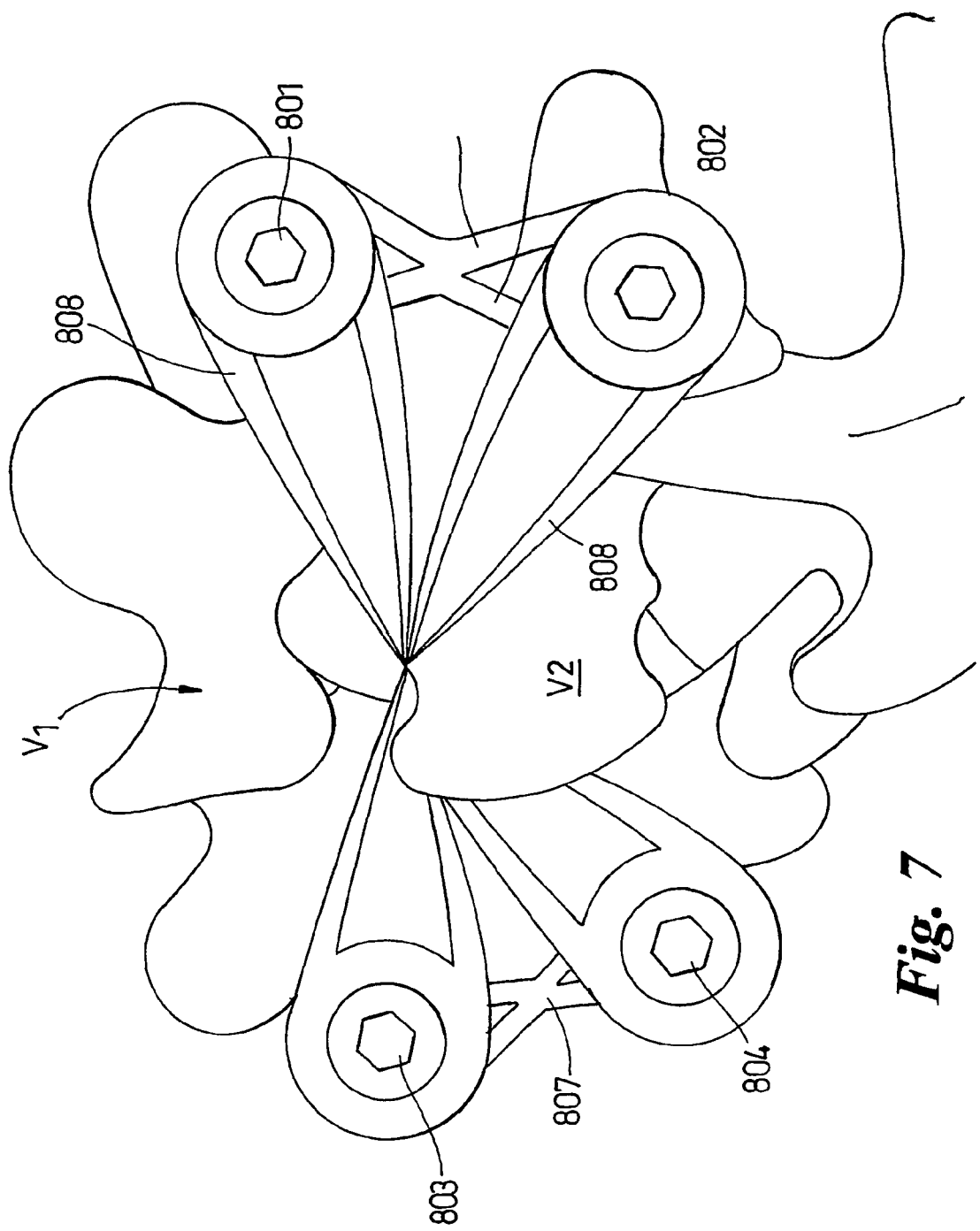
FIG. 7 is a diagrammatic illustration of connectors according to the present invention.

A specific use of connectors according to the present invention is illustrated in FIG. 7 wherein the connector is used as a spinal stabilisation device. In FIG. 7, the connector 800 is shown as being connected to two vertebrae $V_1$, $V_2$ by four pedicle screws 801, 802, 803 and 804. It will be seen that the pairs of screws 801, 802 and 803, 804 located on opposite sides of the vertebrae are each linked by flexible connectors 807 and that they are also linked by transverse connectors 808.

It is to be appreciated that in the connector of the present invention, the load bearing filament 28 is laid along a predefined circuitous path to define adjacent individual strands 28b extending about each aperture with aperture connecting strands 28a and/or 28c extending inbetween adjacent apertures.

The individual strands 28b are laid in a nested arrangement with individual strands held in the nested arrangement at anchorage locations connected to a backing sheet and by binding filaments 30 which bind all the individual strands 28b together. Collectively securance of individual strands 28b at said anchorage locations and binding all the strands 28b together by filaments 30 serve to restrain relative lateral movement between the individual strands 28b when a tensile load is applied between a pair of adjacent apertures. Accordingly, the prime purpose of the anchorage locations and binding filament 30 is to maintain the strands 28b in position and not, themselves, to accommodate the tensile loadings inbetween adjacent apertures.

Accordingly the binding filament 30 and needle sewing thread used for forming the anchorage locations can be of a lighter weight than the load bearing filament 28. Since the binding filament 30 and sewing thread do not form a tensile load bearing function, the bulk size of the connector is, in the main, determined by the amount of load bearing filament 28 required.

This enables the connector of the present invention to be of a relatively small size compared to other known connectors.

Also, since the backing sheet is provided primarily to retain the load bearing strands, in particular strands 28*a*, 28*c* in a disciplined manner for handling purposes during implantation, the flexibility of strands 28*a*, 28*c* is not impeded by the relatively lightweight backing sheet and thereby enables the load bearing strands 28*a*, 28*c* to bend/flex in a smooth manner inbetween adjacent bone anchorage locations.

The invention claimed is:

1. A connector comprising at least one pair of apertures for receiving a fastener, a backing sheet, and at least one load bearing filament extending continuously along a predefined circuitous path which extends between and at least partially around each of said pair of apertures, said load bearing filament including multiple aperture forming strands extending around each aperture, said multiple aperture forming strands of said load bearing filament being supported on said backing sheet and bound together at least partially around each aperture by sewn stitches formed from binding filaments in order to constrain relative lateral movement between said aperture forming multiple strands and to define the shape of each aperture.

2. A connector according to claim 1 wherein said at least one load bearing filament is laid along said predefined circuitous path via embroidery.

3. A connector according to claim 1 wherein said backing sheet comprises at least one of an embroidered article, a knitted fabric, a woven fabric, and a plastic sheet.

4. A connector according to claim 1 wherein said backing sheet is defined by a series of interconnected sewn stitches formed from said binding filaments.

5. A connector according to claim 4 wherein said series of interconnected sewn stitches are arranged to define a backing sheet in the form of a mesh.

6. A connector according to claim 1 wherein said load bearing filament extends along said circuitous path for a plurality of circuits to define multiple strands of said load bearing filament extending between and around each of the apertures of said pair of apertures.

7. A connector according to claim 1 wherein three or more apertures are provided and wherein said circuitous path along which said load bearing filament is laid defines chain links of said load bearing filament which connect pairs of said apertures.

8. A connector according to claim 1 wherein at least one of said binding filament and said load bearing filament is a textile yarn.

9. A connector according to claim 8 wherein said load bearing filament is a textile suture thread of a diametric size between 0.2 to 0.5 mm.

10. A connector according to claim 8 wherein said binding filament is a textile suture thread of a diametric size between 0.1 to 0.2 mm.

11. A connector according to claim 1 wherein said multiple strands defined by the load bearing filament comprise between 2 to 15 strands.

12. A connector according to claim 1 wherein said load bearing filament is a wire formed from a shape-memory alloy.

13. A connector according to claim 1 including a pulling tail or cord.

14. A connector according to claim 1 wherein said aperture forming multiple strands extend completely around each aperture.

15. A connector according to claim 1 wherein said fastener comprises a screw.

16. A connector according to claim 1 wherein said binding filaments extend about at least the outer periphery of said apertures.

17. A connector according to claim 16 wherein said binding filaments extend about the entire periphery of said apertures.

18. A connector according to claim 1 wherein at least one of said load bearing filament and said binding filament is constructed from polyester, polypropylene, polyethylene, polyamide, polylactic acid, and alginate fibers.

19. A connector according to claim 1 wherein said load bearing filament is constructed from at least one of polyester, polypropylene, polyethylene, polyamide, polylactic acid, alginate fibers, metal fibers, aramid fibers, and glass strands.

* * * * *